(12) United States Patent
Rao

(10) Patent No.: US 8,149,407 B1
(45) Date of Patent: Apr. 3, 2012

(54) METHOD AND APPARATUS FOR TRACE GAS DETECTION USING OFF-AXIS CAVITY AND MULTIPLE LINE INTEGRATED SPECTROSCOPY

(75) Inventor: Gottipaty Rao, West Hempstead, NY (US)

(73) Assignee: Adelphi University, Garden City, NY (US)

( * ) Notice: Subject to any disclaimer, the term of this patent is extended or adjusted under 35 U.S.C. 154(b) by 0 days.

(21) Appl. No.: 13/026,011

(22) Filed: Feb. 11, 2011

Related U.S. Application Data

(63) Continuation-in-part of application No. 12/878,553, filed on Sep. 9, 2010.

(51) Int. Cl.
*G01N 21/00* (2006.01)
(52) U.S. Cl. .................................................. 356/437
(58) Field of Classification Search ........... 356/436–438
See application file for complete search history.

(56) References Cited

U.S. PATENT DOCUMENTS 7,541,586 B2 * 6/2009 Miller .................. 250/339.07

* cited by examiner

*Primary Examiner* — Michael P Stafira
(74) *Attorney, Agent, or Firm* — Leason Ellis LLP

(57) ABSTRACT

A sensor for $NO_2$ with ultrahigh sensitivity of detection is created by combining off-axis integrated cavity output spectroscopy (OA-ICOS) (which can provide large path lengths of the order of several km in a small volume cell) with multiple line integrated absorption spectroscopy (MLIAS) (where the absorption spectra is integrated over a large number of rotational-vibrational transitions of the molecular species to further improve the sensitivity). Employing an external cavity tunable quantum cascade laser operating in the 1601-1670 $cm^{-1}$ range and a high finesse optical cavity, the absorption spectra of $NO_2$ over 100 transitions in the R-band have been recorded. Based on the observed linear relationship between the integrated absorption vs. concentration of $NO_2$, the sensor has an effective sensitivity of detection of 28 ppt for $NO_2$, which is among the most sensitive levels of detection of $NO_2$ to date. This technique can be applied using any tunable laser source, such as diode lasers, capable of tuning over multiple lines of target species including complex molecules and explosive compounds.

27 Claims, 5 Drawing Sheets

METHOD AND APPARATUS FOR TRACE GAS DETECTION USING OFF-AXIS CAVITY AND MULTIPLE LINE INTEGRATED SPECTROSCOPY

CROSS REFERENCE TO RELATED APPLICATIONS

This application is a continuation-in-part of prior non-provisional application Ser. No. 12/878,553 filed Sep. 9, 2010 and its contents are incorporated herein by reference. This application is related to non-provisional application Ser. No. 13/025,991 filed on even date herewith.

BACKGROUND OF THE INVENTION

The present invention relates to the detection of trace gas species such as explosives, drugs and steroids with high selectivity and specificity and, more particularly to tunable laser-based systems for trace detection of nitrogen dioxide.

The real-time detection of trace gases in the parts-per-billion ($10^{-9}$) and parts-per-trillion ($10^{-12}$) levels is of great interest in a wide range of fields, including environmental science (e.g., study of complex chemical reactions that take place in the atmosphere, particularly in the presence of solar radiation) and air quality control (e.g., for compliance with Environmental Protection Agency regulations), defense and homeland security (e.g., for the detection of trace amounts of explosive compounds), non-invasive medical diagnostics (e.g., breath analysis), detecting trace impurities in semiconductor material processing and device fabrication, in the food industry (e.g., monitoring ethylene), and optimizing combustion processes and minimizing pollution emissions, to name a few. See the following articles that describe these prior concerns: "Primary National Ambient Air Quality Standards for Nitrogen Dioxide; Final Rule," *Federal Register*, Vol. 75, No. 26, 6474-6537, Feb. 9, 2010; United States Environmental Protection Agency, "National Air Quality Status and Trends Through 2007, EPA-454/R-08-006", United States Environmental Protection Agency, Washington D.C., (2008); J. Hildenbrand, et al., Explosive detection using infrared laser spectroscopy," *Proc. SPIE* 7222, 72220B-1-72220B-12 (2009); T. H. Risby, S. F. Solga, "Current status of clinical breath analysis," *Appl. Phys. B* 85, 421-426 (2006); G. M. Mitchell et al., "Trace Impurity Detection in Ammonia for the Compound Semiconductor Market," Semicon West, San Francisco, Calif., Jul. 17-21, 2002; and A. Arnold et al., "Laser in situ monitoring of combustion processes," *App. Opt.*, 29, 4860-4872 (1990).

Laser-based techniques are well suited for trace gas species detection because of their ability to provide real-time monitoring capabilities with a high degree of sensitivity and selectivity. In particular, quantum cascade lasers (which emit in the mid-infrared region covering 4-24 µm) are especially attractive for this task because they provide access to the fundamental rotational-vibrational transitions of molecular species. See, A. A. Kosterev et al., "Chemical Sensing with pulsed QC-DFB lasers operating at 6.6 µm" *Appl. Phys. B.* 75, 351-357 (2002); F. K. Tittel et al., "Recent Advances in Trace Gas Detection Using Quantum and Interband Cascade Lasers," *Rev. of Laser Eng.* 34, 275-282 (2006); A. Kosterev et al., "Application of quantum cascade lasers to trace gas analysis," *Appl. Phys. B* 90, 165-176 (2008); R. F. Curl et al., "Quantum cascade lasers in chemical physics" *Chem. Phys. Lett.* 487, 1-18 (2010); and a recent comprehensive review article by the present inventor, Gottipaty N Rao along with A. Karpf, "External cavity tunable quantum cascade lasers and their applications to trace gas monitoring," *Applied Optics*, Vol. 50 Issue 4, pp. A100-A115. (2011).

As noted in these articles, quantum cascade lasers have been used to detect several trace gasses, including CO, $CO_2$, NO, $NO_2$, $NH_3$, $CH_4$ and $N_2O$, as well as explosive compounds such as TNT. See the Hildenbrand et al. article. A reliable $NO_2$ monitor capable of high sensitivity and selectivity would be valuable for monitoring atmospheric air quality (to meet EPA air quality standards, and monitor the formation of photochemical smog, tropospheric ozone, and automobile and industrial emissions), as well as for the real-time study of the complex photochemical reactions that $NO_x$ gases undergo in the atmosphere.

A variety of spectroscopic techniques have been developed for detection, each having its own merits and limitations. The spectroscopic techniques that are commonly employed include, absorption spectroscopy using long pass absorption cells such as multipass and Herriott cells, optical cavity methods (cavity ring-down spectroscopy, off-axis integrated cavity output spectroscopy), photo-acoustic and quartz-enhanced photo-acoustic spectroscopy, and Faraday rotation spectroscopy. Various data processing and analysis procedures are followed such as frequency modulated spectroscopy techniques to improve the signal to noise ratio and multiple line integrated absorption spectroscopy to improve the sensitivity of detection. The current status of much of this work was presented in the recent review article by the present inventor Gottipaty N Rao and by A. Karpf, and the conference presentations Gottipaty N Rao et al., "Sensors at ppb Sensitivity or Better Based on Multiple Line Integration Spectroscopy Techniques," *Laser Applications to Chemical, Security and Environmental Analysis* (*LACSEA*) 2010 paper: LPDP2; Gottipaty N Rao et al., "A Trace Gas Sensor at ppb Sensitivity Based on Multiple Line Integration Spectroscopy," *Conference on Lasers and Electro-Optics* (*CLEO*) 2010 paper: JWA60, as well as the inventor's co-pending U.S. patent application Ser. No. 12/878,553 filed on Sep. 9, 2010, and which is incorporated herein in its entirety.

External cavity tunable quantum cascade lasers are quite compact, operate at room temperatures, have large operating lifetimes, require low power levels for operation, provide reasonably high output powers with a narrow laser line width, and can be operated over a widely tunable range (hundreds of wave numbers), which makes them well suited for trace gas monitoring applications in real time. They are also amenable to fiber optic technology and therefore can be employed for remote monitoring applications. Trace gas detection using laser absorption spectroscopy is based on recording the change in intensity of laser radiation as it passes through a region containing the sample of interest. In this technique, often the laser is rapidly swept across specific molecular transitions of interest, the spectra are synchronously added and averaged, and compared with the molecular cross-section data or employ secondary calibration procedures to obtain the concentrations. In order to detect very low concentration species in the ppb level or lower, multi-pass cells can be employed to increase the path length and improve the sensitivity of detection. Using multipass optical cells, one can reach path lengths in the hundreds of meters range; however, the volume of these cells is large (typically about 1 l). The main difficulty with multipath cells is that they are bulky, involve careful cavity adjustments and are sensitive to vibrations which are potential limitations for field applications. Fabry-Perot optical cavities provide long path lengths on the order of several km in a small effective volume. See A.

O'Keefe et al., "CW Integrated Cavity Output Spectroscopy," *Chem. Phys. Lett.*, 307, 343-349 (1999); R. Engeln et al., "Cavity enhanced absorption and cavity enhanced magnetic rotation spectroscopy, *Rev. Sci. Instrum.* 69, 3763 (1998); J. B. Paul et al., "Ultrasensitive absorption spectroscopy with a high-finesse optical cavity and off-axis alignment," *Appl. Opt.* 40, 4904-4910 (2001); and G. Berden et al., "Cavity ring-down spectroscopy: Experimental schemes and applications," *Int. Reviews in Physical Chemistry*, Vol. 19, No. 4. 565-607 (2000). In this technique, the laser is coupled to a high finesse optical cavity (formed by highly reflective, low-loss dielectric mirrors) so that a large amount of light energy builds up within the cavity. In cavity ringdown spectroscopy (CRDS), one interrupts the laser beam and measures the exponential decay of the light exiting the cavity (cavity ring-down time) with and without the gas sample. While, CRDS offers high sensitivity of detection and provides an absolute value of the concentration of the species (i.e., no need for secondary calibration procedures), it is susceptible to vibrations and requires stringent cavity resonance conditions.

SUMMARY OF THE INVENTION

The present invention is directed to improving the accuracy of the detection of trace gases by employing off-axis integrated cavity output spectroscopy coupled with multiple line integrated spectroscopy.

According to the present invention, off-axis integrated cavity output spectroscopy ("OA-ICOS") is used to provide a path length of several km. In this technique, the laser is aligned in an off-axis configuration to generate a high density of transverse cavity modes. The cavity length is dithered and the laser is simultaneously modulated to randomize the modes and record usable spectra. The OA-ICOS technique is particularly attractive for trace gas species sensors because the system does not involve the complex cavity locking mechanisms or stringent resonance conditions necessary in cavity ring-down spectroscopy ("CRDS"), and is less sensitive to vibrations. The off-axis arrangement allows a range of laser input directions compared to a single normal incidence condition that is necessary for the cavity resonance condition. Therefore, the off-axis arrangement allows a certain level of freedom from the severe vibration isolation and cavity alignment requirements of the cavity resonance techniques, such as CRDS. When using mid-infrared lasers, ICOS offers an additional advantage over CRDS in that it is less susceptible to problems related to optical feedback and the associated laser output instabilities. It has been found by the present inventor that optical feedback is a major problem in mid-infrared laser based work, since optical isolators are not commercially available in this region.

According to the present invention, OA-ICOS is coupled with multiple line integrated absorption spectroscopy (MLIAS) See the present inventor's co-pending U.S. patent application Ser. No. 12/878,553 filed on Sep. 9, 2011. Also see the inventor's articles A. Karpf, G. N. Rao, "Enhanced Sensitivity for the Detection of Trace Gases Using Multiple Line Integrated Absorption Spectroscopy," *Appl. Opt.*, 48, 5061-5066 (2009); and A. Karpf, G. N. Rao, "Enhancement of Trace Gas Detection by Integrating Wavelength Modulated Spectra across Multiple Lines," *Appl. Opt.*, 49, 1406-1413 (2010), which are incorporated herein by reference in their entirety. In this technique, instead of monitoring a single absorption peak as is traditionally done, the laser is scanned over a large number of rotational-vibrational transitions and the sum of the areas of all the absorption peaks is used (after subtracting the background) for sensitivity measurements. Employing this method, the sensitivity of detection can be significantly improved.

Off-Axis Integrated Cavity Output Spectroscopy (OA-ICOS)

In cavity enhanced absorption spectroscopy techniques, a tunable laser and a high finesse optical cavity are employed and the cavity output is observed while tuning the laser over the wavelength range of interest. These techniques are known in the literature as integrated cavity output spectroscopy (ICOS) and cavity enhanced absorption spectroscopy (CEAS). In an Off-Axis ICOS, the laser is aligned in an off-axis configuration to create an extremely dense continuum of optical modes within the cavity. The continuum of modes allows for the more effective averaging of the cavity transmission spectrum, resulting in significant improvement in the sensitivity of detection. See J. H. Van Helden et al., "Cavity Enhanced Techniques Using Continuous Wave Lasers." in *Cavity Ring-down Spectroscopy*, (eds.) G. Berden and R. Engeln, Wiley, (2009), pp. 27-56, which is incorporated herein by reference in its entirety.

In CRDS the optical cavity is carefully aligned such that the $TEM_{00}$ mode is dominant. This is accomplished by aligning the laser beam so that it coincides with the cavity axis. As the laser is tuned the resonance condition is satisfied, the cavity output is characterized by sharp spikes separated by the free spectral range (FSR) of the cavity; and the width of the spike depends on the cavity finesse. In the case of OA-ICOS, the laser beam is incident at a small angle with respect to the cavity axis resulting in a large number of cavity modes including $TEM_{00}$, $TEM_{01}$, $TEM_{02}$, . . . $TEM_{mn}$. The cavity transmission spectra thus consist of a large number of spikes at frequencies corresponding to the different modes. The intensity of the transmitted peaks depends on the overlap between the laser and the cavity modes. At higher modes ($TEM_{mn}$) the cavity FSR gets (n+m) times smaller compared to the $TEM_{00}$ mode and the density of modes increases. Y. A. Bakhirkin et al., "Sub-ppbv nitric oxide concentration measurements using CW thermoelectrically cooled quantum cascade laser-based integrated cavity output spectroscopy," *Appl. Phys. B* 82, 149-154 (2006). In OA-ICOS, the cavity is carefully misaligned to have a continuum of very high density cavity modes. At the same time it must be assured that the beam undergoes a large number of multiple reflections in the cavity, thus ensuring a long path length before the reentrant condition is reached. If an absorbing gas species is present in the cavity, as the laser is tuned, absorption spectra specific to the species can be observed. The signal-to-noise ratio of a single scan spectrum is often not satisfactory because the cavity modes are not completely random, resulting in mode noise. Therefore, dithering one of the mirrors of the cavity and/or modulating the laser frequency and averaging over multiple scans affectively randomizes the mode structure and thus significantly improves the signal-to-noise ratio, resulting in a transmission spectra that corresponds to the characteristic absorption lines of the gas species. M. L. Silva et al., "Integrated cavity output spectroscopy measurements of nitric oxide levels in breath with a pulsed room-temperature quantum cascade laser," *Appl. Phys. B* 81, 705-710 (2005) and A. Kosterev et al., "Application of quantum cascade lasers to trace gas analysis," *Appl. Phys. B* 90, 165-176 (2008).

A variety of cavity configurations can result in stable off-axis path lengths through a cavity. For a two mirror cavity with spherical mirrors, the test arrangement must satisfy the stability condition set forth in A. Kosterev et al. "Application of quantum cascade lasers to trace gas analysis," *Appl. Phys. B* 90, 165-176 (2008):

$$0 \leq \left(1 - \frac{L}{R_1}\right)\left(1 - \frac{L}{R_2}\right) < 1, \quad (1)$$

where L is the mirror spacing (50 cm). Two spherical mirrors with identical radii of curvatures ($R_1=R_2=1$ m) are used with reflection coefficients R=0.9998. For spherical mirrors, the multiple reflections appear as a series of spots in an elliptical pattern on the mirrors. The pattern becomes re-entrant when $2m\theta=2n\pi$, where θ is the rotation per pass which solely depends on the mirror spacing and radii of curvature of the mirrors, m is the number of round trip passes and n is an integer. The number of passes n depends on the geometry of the cavity and can vary anywhere from a few passes to infinity. The number of passes m is optimized so that, as m increases, the effective path length of the cavity increases and the FSR of the cavity decreases.

For a cw laser, under the steady state conditions, the intracavity power may be written as:

$$I = \frac{I_0 C_p T}{2(1-R)}\left(1 - e^{\frac{-t}{\tau_0}}\right), \quad (2)$$

where $I_0$ is the incident laser intensity, $C_p$ is the cavity coupling parameter (it has a value between 0 and 1 and can reach 1 for a well matched $TEM_{00}$ mode), R is the reflectivity of the mirrors (assumed constant for both the mirrors) and T is the transmission coefficient of the mirrors (again assumed constant for both the mirrors), $\tau_o$ is the cavity ring-down time. See the Paul et al. article. The cavity ring-down time is given by:

$$\tau_0 = \frac{L}{c(1-R)}. \quad (3)$$

Here L is the distance between the mirrors and c is the speed of light. From Eq. (2), the steady state condition is given by:

$$I = \frac{I_0 C_p T}{2(1-R)}. \quad (4)$$

Approximately half of this intensity will leak through each of the cavity mirror.

With an absorbing medium between the mirrors, R is replaced with R':

$$R' = Re^{-L\alpha(\nu)}, \quad (5)$$

where $L\alpha(\nu)$ is the absorbance of the medium in the cavity. This shows that the absorbance information is contained in the steady state cavity intensity which can be measured. The change in the steady state output of the cavity due to the presence of the absorbing species in the cavity may be expressed in the form:

$$\frac{\Delta I}{I_0} = \frac{GA}{1+GA}, \quad (6)$$

where $A = 1 - e^{-L\alpha(\nu)}$ and $G = R/(1-R)$. Therefore, for weak absorption, the cavity provides a large linear gain in the absorption signal. In Eq. (6), for trace gas species, GA<<1 and can be neglected in the denominator. Eq. (6) may be written in the form:

$$\frac{I_0(\nu) - I(\nu)}{I_0(\nu)} = \frac{\alpha(\nu)L}{(1-R)}. \quad (7)$$

The relative change in the laser intensity is directly proportional to the absorption coefficient and hence the number density of the trace species. The ICOS steady state cavity output intensity is recorded as a function of the frequency as the laser is tuned.

Multiple Line Integrated Absorption Spectroscopy (MLIAS)

As the laser is tuned across a transition, the transmitted laser intensity is a function of frequency ν given by Beer's law:

$$I(\nu) = I_0(\nu)e^{-\alpha(\nu)L}, \quad (8)$$

where $I_0$ is the incident laser intensity, L is the optical path length, and $\alpha(\nu)$ is the absorption coefficient at frequency ν. J. M. Hollas, *High Resolution Spectroscopy*, Second Edition, (Wiley 1998). In the low concentration regime (where $\alpha(\nu)L \leq 0.05$) one can approximate Eq. (8) as:

$$I(\nu) = I_0(\nu)[1 - \alpha(\nu)L]. \quad (9)$$

The sensitivity of a spectrometer is often determined by taking the ratio of the amplitudes of the absorption line to that of the noise level.

Using an absorption line's amplitude to detect a species, however, neglects the width of the line and as a result gives the same intensity for both broad and narrow lines with the same amplitude. For example, even though a sample of $NO_2$ at 600 mbar has twelve times more molecules than the same sample at 50 mbar, its absorption spectrum shows only about a 25% enhancement in peak absorption: The majority of additional absorption manifests itself in the broadening of the lines. As a result, when dealing with broadened lines a more accurate measure of the absorption intensity can be achieved by using the area under the absorption curve instead of the amplitude. Assuming that $\alpha(\nu)L$ is small (as is typically the case with trace gas detection), the integrated absorption may be written as:

$$S = \int \alpha(\nu)L d\nu. \quad (10)$$

For a single transition, the absorption coefficient $\alpha(\nu) = \sigma(\nu)N$ (where $\sigma(\nu)$ is the cross-section and N is the concentration). The cross section depends on the Einstein A coefficients of the levels and the statistical weight factors. The integral is to be carried out over Doppler and collisional broadened line shape functions. Thus the integrated absorption is proportional to the concentration N. While, each of the absorption peaks is a complex function as detailed above, a test parameter $S_T$, which is equal to the number density $N_i$ multiplied by the sum of the areas under the different absorption peaks, can be defined. Based on this, it can be shown that the sum of the areas of a set of absorption lines varies linearly with concentration, and conducting trace gas detection by integrating over multiple absorption lines can enhance the sensitivity of a detector by over one order of magnitude. See the inventor's article, A. Karpf, G. N. Rao, "Enhanced Sensitivity for the Detection of Trace Gases Using Multiple Line Integrated Absorption Spectroscopy," *Appl. Opt.* 48, 5061-5066 (2009). The sum of the areas of multiple absorption lines may be defined as the test parameter $S_T$ and measured for different concentrations of the target species:

$$S_T = \sum_i \int \alpha_i(v) L dv. \quad (11)$$

Here, $\alpha_i(v)$ is the absorption coefficient of the ith transition of the target species, and the summation is over all transitions within the selected tuning range of the detector. Using pre-calibrated reference mixtures of the desired gas, an $S_T$ vs. concentration curve can be defined that characterizes a particular apparatus (e.g., this would take into account the optical path length L, the tuning range and other equipment-related factors and as well as the Einstein A coefficients and the statistical weight factors and the Doppler and the collisional broadened absorption lines). Unknown concentrations of the species can be identified by recording their $S_T$ and identifying their corresponding concentrations on this curve.

This procedure enhances the sensitivity of detection in three ways. The first enhancement is due to the summing of the areas under many spectral lines (which boosts the magnitude of the recorded signal). The second enhancement is from the fact that the integration has the effect of averaging the random components of the noise. Due to the fact that this data is acquired in a single scan (which can take less than a second), this effective averaging of the noise occurs in a shorter time span than would be the case for averaging the signal by adding repeated fast scans. The third enhancement in sensitivity over standard laser absorption techniques is that it is not limited to working in the low-pressure regime (i.e., there is no need to resolve the lines individually). This procedure is particularly valuable for molecules which have a large number of transitions grouped together.

Thus the present invention provides a powerful new technique for the detection of trace species with high sensitivity and specificity. This technique is applicable for the detection of trace molecular species, explosive compounds, steroids and drugs with very high sensitivity and selectivity and can be employed for field based applications as well. The invention combines off-axis integrated cavity output spectroscopy (OA-ICOS) (which can provide large path lengths of the order of several km in a small volume cell) with multiple line integrated absorption spectroscopy (MLIAS) (where integration is performed over a large number of absorption features to further improve the sensitivity). The potential of the technique is demonstrated by recording the absorption features of $NO_2$ over 100 transitions in the R-band employing an external cavity tunable quantum cascade laser operating in the 1601-1670 $cm^{-1}$ range and a high finesse optical cavity. From the observed linear relationship between the integrated absorption vs. concentration of $NO_2$, an effective sensitivity of 28 ppt (parts per trillion) detection sensitivity for $NO_2$ is obtained. This is among the most sensitive levels of detection of $NO_2$ to date. An important feature of this new technique is that it is not sensitive to vibrations and can be employed for field based applications.

BRIEF DESCRIPTION OF THE DRAWINGS

The foregoing and other features of the present invention will be more readily apparent from the following detailed description and drawings of an illustrative embodiment of the invention in which.

DESCRIPTION OF AN ILLUSTRATIVE
EMBODIMENT OF THE INVENTION

Figure 1:
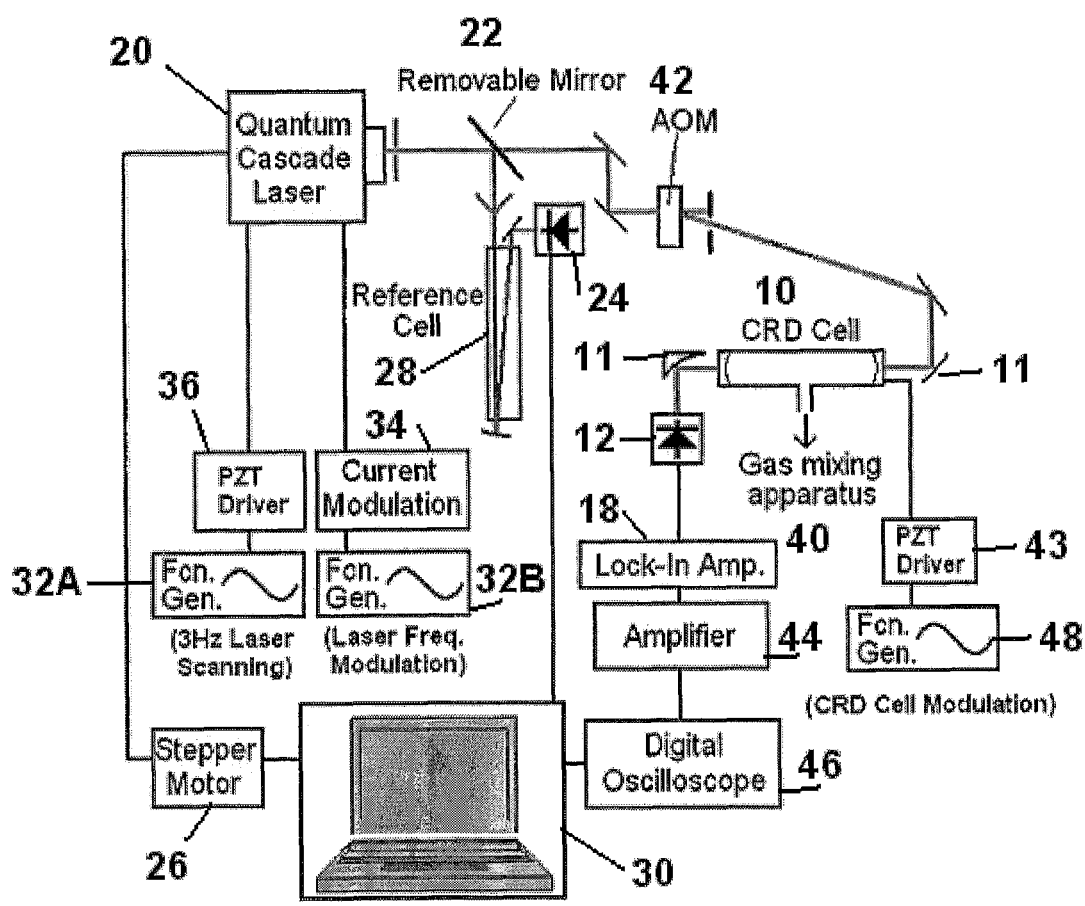
FIG. 1 a block diagram of the apparatus for multiple-line integrated absorption spectroscopy with off-axis integrated cavity output spectroscopy for the detection of trace amounts of $NO_2$.

According to the present invention and as shown in FIG. 1, Integrated Cavity Output Spectroscopy of $NO_2$ is carried out using a Continuous Wave Quantum Cascade Laser (QCL). A suitable QCL is available from Daylight Solutions (Model TLS-CW-MHF). The QCL uses an external cavity (comprised of a diffraction grating aligned in a Littrow configuration), to provide a wide range of mode hop-free tuning (1604 $cm^{-1}$ to 1670 $cm^{-1}$) and a narrow line width (~0.001 $cm^{-1}$), which is well suited for spectroscopic measurements.

FIG. 1 shows a Quantum Cascade laser 20, the output of which is directed on to a beam splitter 22. One part of the beam is reflected downwardly in the drawing to a reference cell 28. The other part of the beam travels through the beam splitter and enters an acousto-optic modulator ("AOM") 42 that chops the laser beam into laser beam pulses. The laser pulses enter a cavity ring down (CRD) cell 10, where it makes a sufficient number of round trips by bouncing off high reflectivity mirrors 11, 11A, that the effective path length is about 2 km. Upon leaving the cell the laser pulses enter a photodetector 12. The photodetector may be a two-stage, TE-cooled, IR photovoltaic detector (e.g., the PVI-2TE-8 manufactured by Vigo), which can be operated in a room-temperature environment. This and other detectors used in this apparatus may be optically immersed in a high refractive index, hyperhemispherical lens that is part of the detector package.

The output of detector 12 is applied to a Lock-In amplifier 18 that is a phase sensitive detector, i.e., it can be tuned to detect the signals at the laser chopping frequency or its harmonics. The lock-in amplifier 18 may be e.g., a Stanford Research Systems SR830DSP) with the time constant set to 1 ms. The output of the Lock-in amplifier is fed to a linear amplifier 44, the output signal of which is connected to a fast digital oscilloscope and display, and then to computer 30 for measurement and storage.

In the other beam path, which is called the reference beam path, the laser beam reflected from beam splitter 22 enters a reference cell 28. After leaving the reference cell the laser beam is received by detector 24. The signal of the detector 24 is connected to computer 30 and can be subtracted from the signal from the CRD cell 10.

The stepper motor 26 rotates the external cavity grating of the laser 10 to tune the laser over a frequency range that covers the absorption features of the species of interest. The difference signals summed over multiple absorption features of the species as calculated from the data on the computer 30 is specific to the particular species of interest and is directly related to the amount of trace gas species in the sample. The great accuracy of the present invention is achieved in part by extending the path length with the multi-pass cavity ring down cell 10 and then summing the data over many absorption features of the species by tuning the laser.

The laser power varies as a function of tuning, with a minimum output power of 14 mW at 1604 cm$^{-1}$, and a maximum of 21 mW at 1640.4 cm$^{-1}$. The output power at 1656 cm$^{-1}$ (the frequency at which measurements are made) was 17 mW. The laser could be tuned using three different methods. Course tuning (over the entire range of the QCL) was accomplished using the stepper motor 26 to rotate the diffraction grating. A piezo electric driver or transducer (PZT) 36 allows for fine tuning of the diffraction grating over a 2 cm$^{-1}$ range. In particular, a function generator 32A, which can be a Stanford Research Systems DS345 function generator, creates a triangle wave form to drive the PZT 36 and tune the laser over a 2 cm$^{-1}$ range at a frequency of 3 Hz. Additionally, high frequency tuning over a smaller 1 cm$^{-1}$ range is available via current modulation circuit 34. In particular, a high frequency sinusoidal signal from function generator 32B drives current modulation circuit 34, whose current output is applied to the laser head to modulate its frequency.

The CRD Cell 10 was constructed using components and mirrors purchased from Los Gatos Research. The cell is 50 cm long, and has mirrors with a radius of curvature of 1 meter, and a reflectivity of 99.98% at 1650 cm$^{-1}$. The cell was connected to a vacuum system 40 that allowed it to be loaded with different concentrations of the sample species (See FIG. 1).

Phase-sensitive detection was done using an IntraAction model AGM-402A6/11 Acousto-Optic Modulator (AOM) 42 to chop the QCL beam at a frequency of 5 kHz. The mid-infrared radiation laser beam exiting the cell 10 was focused onto a detector 12 using an off-axis paraboloidal reflector 11. The detector is a two-stage, TE-cooled, IR photovoltaic detector (PVI-2TE-8 manufactured by Vigo). It was operated in a room-temperature environment. Further, the detector was optically immersed in a high refractive index, hyperhemispherical lens that is part of the detector package.

The signal from detector 12 was fed to a lock-in amplifier 18 (which may be a Stanford Research Systems SR830DSP). The lock-in time constant was set to 3 ms. The signal from the lock-in amplifier was fed to a scaling amplifier 44 (which may be a Stanford Research Systems SIM983), and then to a digitizing oscilloscope 46, which may be a Tektronix DP03034. The oscilloscope output was fed to a PC 30 via a USB connection and the signal was recorded on the PC using Tektronix software.

The AOM 42 chopping frequency for lock-in detection was selected based on the ring down time of the CRD cell. The ring down time for an empty cell was measured by precisely aligning the cavity mirrors with the incoming QCL beam to form a standing wave: This resulted in a large energy build-up within the cavity. The input light was interrupted using the high-speed AOM chopper and the exponential decay time of the light exiting the cavity (known as the ring down time) was measured. For an empty cavity the ring down time depends on the reflectivity of the mirrors, and is given by:

$$\tau_0 = \frac{L}{c(1-R)}. \quad (3)$$

where R is the mirror reflectivity, and L is the distance between the cavity's mirrors. The ring down time for the CRD cell was measured to be 8.7±0.15 µs, which corresponds to the mirrors' stated reflectivity of 99.98%. The chopping frequency of 5 kHz was selected such that the duration of a pulse was over an order of magnitude longer than the ring down time, and thus did not interfere with the averaging of the cavity output for ICOS. The signal-to-noise ratio was tested for a variety of chopper frequencies between 1 kHz and 20 kHz, with the optimal signal-to-noise ratio occurring at approximately 5 kHz.

The off axis alignment did not result in a continuum mode structure (i.e. in complete averaging of the cavity modes) and resulted in mode noise in the ICOS spectrum, thus requiring further averaging by modulating both the laser frequency and the CRD cell length. When modulating the laser frequency it was necessary to assure that the overlap time of the laser frequency with the cavity resonance was insufficient for the cavity to reach a saturation resonance condition. Based on the line width of the Daylight Solutions QCL (Δv~40 MHz) and the Free Spectral Range (FSR) of the cavity ring down cell (300 MHz), the laser line was modulated at a frequency of 50 kHz. This was done by feeding a sine wave signal from function generator 32B into a current modulator 34, which in turn delivered a current modulated input to the laser head of the QCL. The function generator may be a Stanford Research Systems model DS345 function generator. The amplitude of the sine wave was chosen such that modulation of the laser line spanned one FSR of the CRD cell. The CRD cell length was modulated at a frequency of 300 Hz by using a sine wave generated by another function generator 48 that drove a piezo driver or controller 43. The function generator 48 may be another DS345 function generator and the piezo driver may be a Thorlabs model MDT693A piezo controller. The amplitude selected for the 300 Hz sine wave corresponds to modulating the CRD cell over one FSR. The signal-to-noise ratio was tested for a variety of laser modulation frequencies (between 10 kHz and 1 MHz) and a variety of CRD cell length modulation frequencies (between 10 Hz and 500 Hz), with the optimal signal occurring for the values specified above.

The NO$_2$ mixtures were prepared by loading the test cell with a pre-calibrated mixture of NO$_2$ in Zero Air (a mix of 20.9% O$_2$ and 79.1% N$_2$). The pre-calibrated NO$_2$ mixture had a concentration of 5 ppm and was certified by Gasco Affiliates, LLC to ±10% of the specified concentration. The concentrations used in testing the system were created by loading the cell with the 5 ppm mixture to a certain pressure, and then adding Zero Air to increase the pressure to the desired final value (1000 mbar). For example, a 250 ppb concentration was generated by first loading the test cell with 50±10 mbar of the pre-calibrated 5 ppm mix of NO$_2$ before additional Zero Air was added to reach a final pressure of 1000±10 mbar. Due to limitations in the accuracy of the vacuum/mixing apparatus, the concentrations prepared are believed to be accurate to ±20% (e.g., a 250 ppb concentration mixture is expected to contain between 200 and 300 ppb NO$_2$). The mixing apparatus was tested by generating several concentrations of NO$_2$, and comparing the recorded absorption spectra with simulated spectra generated using the HITRAN database and the SPECTRA software developed by Mikhailenko, et al. See L. S. Rothman et al., "The HITRAN 2004 molecular spectroscopic database", *J. Quant. Spectrosc. Radiat. Transfer*, 96 139-204 (2005) and C. N. Mikhailenko et al., "Information-calculating system Spectroscopy of Atmospheric Gases, the structure and main functions," *Atmos. Oceanic Opt.* 18, 685-695 (2005). This confirmed that the mixtures were within the expected range of uncertainty.

Due to the limitations of the gas mixing apparatus, it was not possible to reliably mix concentrations lower than about 100 ppb. Thus, lower concentrations of NO$_2$ were simulated by conducting ICOS on a set of absorption lines whose multiple-line integrated absorption signal was 160 times weaker than the signal calculated for the strongest lines in the $NO_2$ R-branch. The strongest lines in the R-branch are located in the region between 1629.7 $cm^{-1}$ and 1631.7 $cm^{-1}$, and are comprised of nearly 200 closely spaced transitions. The peak absorption in this region is due to two very closely spaced doublets located at approximately 1630.33 $cm^{-1}$; all four lines in these doublets are grouped within 0.003 $cm^{-1}$ (the doublets are identified in Table 1). The lines which were used to test the system were located between 1655.3 $cm^{-1}$ and 1657.3 $cm^{-1}$ (see FIG. 2). They are comprised of approximately 115 closely spaced transitions, of which 34 could be said to contribute significantly to the spectrum (i.e., have transition strengths over 10% that of the strongest transition selected in the tuning range). Table 2 identifies the seven strongest doublets that contribute to absorption in the target region. The comparison of the strengths of the multiple-line integrated absorption signal from the strongest lines in the $NO_2$ R-branch and the multiple-line integrated absorption signal from the weaker target region was carried out using simulated spectra generated using the HITRAN database and the SPECTRA software. By conducting ICOS on this weaker region the effective concentrations of $NO_2$ of the mixtures used for the tests were: 11.9 ppb, 8.4 ppb, 6.3 ppb, 4.7 ppb, 3.1 ppb and 1.6 ppb.

TABLE 1

Spectral Line parameters from HITRAN for the major $NO_2$ doublets that are responsible for the peak absorption in the R-branch.

| Central Freq. of Doublet ($cm^{-1}$) | Upper State $(v_1\ v_3\ v_3)$-$(N'\ K'_a\ K'_c)$ | Lower State $(v_1\ v_3\ v_3)$-$(N''\ K''_a\ K''_c)$ |
|---|---|---|
| 1630.326 | (0 0 1)-(17 1 16) | (0 0 0)-(16 1 15) |
| 1630.328 | (0 0 1)-(17 0 17) | (0 0 0)-(16 0 16) |

TABLE 2

Spectral Line parameters from HITRAN for the strongest $NO_2$ doublets in the target region (between 1655.3 $cm^{-1}$ and 1657.3 $cm^{-1}$).

| Central Freq. of Doublet ($cm^{-1}$) | Upper State $(v_1\ v_3\ v_3)$-$(N'\ K'_a\ K'_c)$ | Lower State $(v_1\ v_3\ v_3)$-$(N''\ K''_a\ K''_c)$ |
|---|---|---|
| 1655.315 | (0 0 1)-(58 1 58) | (0 0 0)-(57 1 57) |
| 1655.456 | (0 0 1)-(57 1 56) | (0 0 0)-(56 1 55) |
| 1655.563 | (0 0 1)-(57 2 55) | (0 0 0)-(56 2 54) |
| 1655.894 | (0 0 1)-(59 0 59) | (0 0 0)-(58 0 58) |
| 1656.301 | (0 0 1)-(60 1 60) | (0 0 0)-(59 1 59) |
| 1656.410 | (0 0 1)-(59 1 58) | (0 0 0)-(58 1 57) |
| 1656.596 | (0 0 1)-(59 2 57) | (0 0 0)-(58 2 56) |

Figure 2:
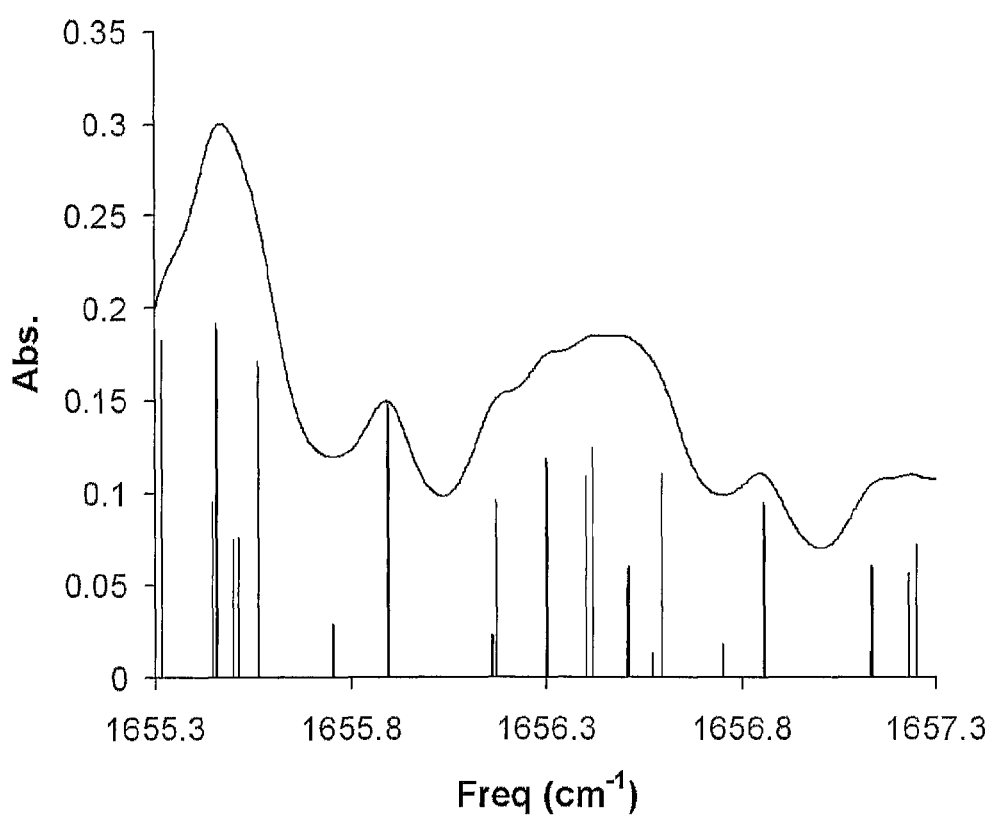
FIG. 2 is a simulated absorption spectrum of $NO_2$ between 1655.3 $cm^{-1}$ and 1657.3 $cm^{-1}$ at a pressure of 1000 mbar.

The simulated absorption spectrum of $NO_2$ between 1655.3 $cm^{-1}$ and 1657.3 $cm^{-1}$ at a pressure of 1000 mbar (the pressure at which trace gas detection was conducted) is shown in FIG. 2. Included in this figure is a "stick" spectrum identifying the individual transitions (and their relative strengths) which lead to the absorption spectrum. It should be noted that transitions that appear to be represented by dark bars are actually very closely spaced doublets.

There were two main factors that needed to be considered for the selection of a region to carry out trace gas detection using multiple line integrated absorption spectroscopy: 1) select a region with a strong dense spectrum, and 2) select a region free from interference due to other species. As mentioned above, the region used for this embodiment (1655.3 $cm^{-1}$ to 1657.3 $cm^{-1}$) contains about 115 closely spaced lines, and thus meets the first requirement. A review of the component species present in the atmosphere and the species included in the HITRAN database shows that only $H_2O$ and $NH_3$ have transitions in this region that are potentially strong enough to cause interference. However the effects of $NH_3$ could be ignored due to the following reasons: 1) the expected concentration of $NH_3$ in ambient air (away from significant forest, industry or farm sources) is in the 10 ppb-100 ppt range; 2) purified $NO_2$ samples mixed with Zero Air used in practicing the invention have insignificant amounts of $NH_3$; 3) the 1 meter beam path from the laser to the cell 10 is 3 orders of magnitude shorter than the effective beam path in the CRD cell; 4) there are an order of magnitude fewer $NH_3$ transitions than $NO_2$ transitions in the target region (between 1655.3 $cm^{-1}$ and 1657.3 $cm^1$). It is believed that the contributions to the observed signal from $NH_3$ are several orders of magnitude smaller than the signal from $NO_2$ and remain constant for all the $NO_2$ concentration measurements (since $NH_3$ contribution would be only from the ambient air outside the cell). Therefore, the effect of $NH_3$ on the present invention can be neglected. It should be noted that the contributions from $NH_3$ can be neglected even when $NO_2$ is monitored in the ambient air. In this case, an investigation would be conducted on the absorption of the intense R-band transitions, the intensity of which are over an order of magnitude larger than the most prominent transitions of $NH_3$ in that region and the number of $NO_2$ transitions are over a magnitude larger than the number of $NH_3$ transitions in the same region.

Figure 3:
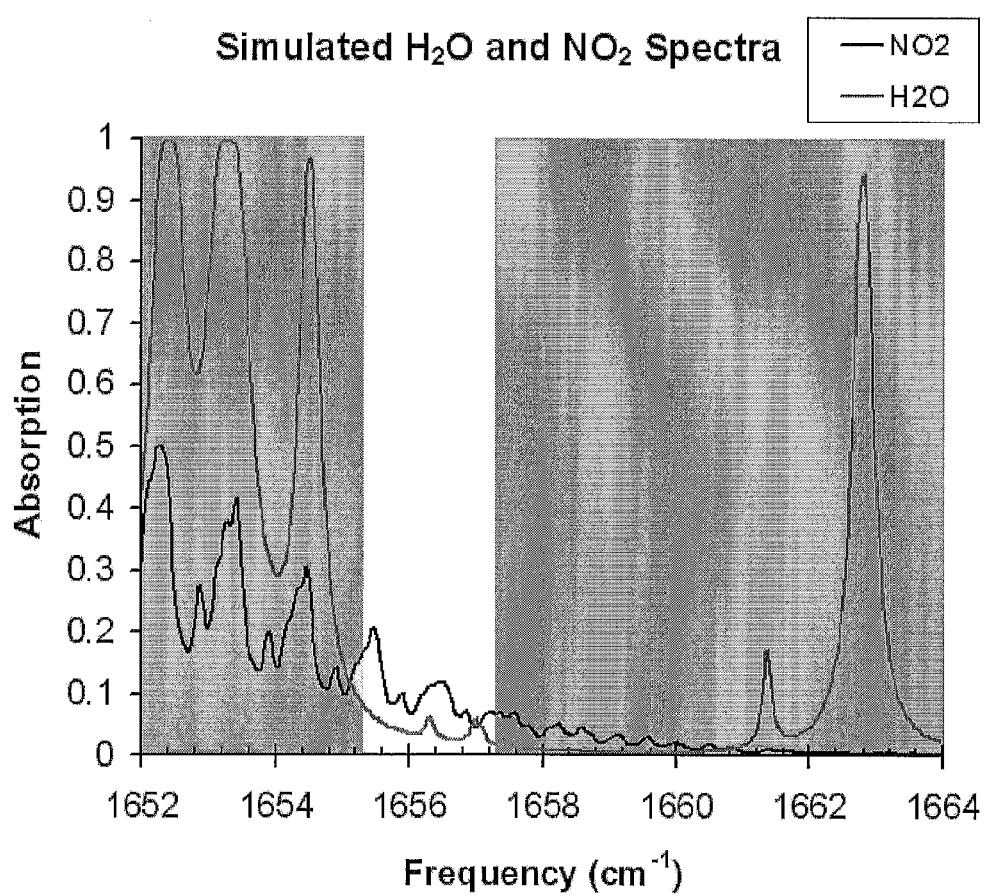
FIG. 3 is a simulated spectrum illustrating where water lines overlap and thus overwhelm any potential $NO_2$ signal in the target region.

The strength of the water lines, however, necessitated the selection of a region in which they do not significantly interfere with recording $NO_2$ spectra. FIG. 3 shows a simulated spectrum illustrating where the water lines (due to ambient water vapor in the beam path leading to the test cell) overlap and thus overwhelm any potential $NO_2$ signal in the target region. Due to the broad width of these water lines, the ability to record relatively weak $NO_2$ spectra is limited to the region between 1655 $cm^{-1}$ and 1660 $cm^{-1}$. As mentioned earlier, the PZT tuning characteristics of the laser limit the tuning range to 2 $cm^{-1}$, thus a 2 $cm^{-1}$ region within this range is selected. The 1655.3 $cm^{-1}$ and 1657.3 $cm^{-1}$ region was selected because it was far enough from the strong water line at 1654.5 $cm^{-1}$ (due to the transition between the (0 1 0)-(5 2 3) and (0 0 0)-(5 1 4) levels) to avoid interference, yet included $NO_2$ lines that were not too weak. The two water lines that were in the target region (located at 1656.3 $cm^{-1}$ and 1657.1 $cm^{-1}$, due to the transitions between the (0 1 0)-(6 4 3) and (0 0 0)-(5 5 0) levels and the (0 1 0)-(6 4 2) and (0 0 0)-(5 5 1) levels, respectively) were weak enough that they did not overwhelm the $NO_2$ signal. Additionally, since the water vapor in the beam path leading to the test cell remained constant for all $NO_2$ concentrations used, the effects of these water lines were subtracted from the recorded $NO_2$ signal (as part of a 0 ppm background measurement).

With the invention, the possible effect of the water vapor continuum absorption was not taken into account. However, it should be stated that the line positions and line intensities calculated using the HITRAN data for water vapor contributions agreed well with the test results. The strength of the water lines was selected to match typical conditions in the mid-latitude U.S. during the winter months (the water vapor density used was 3.46 $g/m^3$ which corresponds to a relative humidity of 68% at 1° C., and is the average relative humidity in Washington D.C. in January). The strength and width of the water lines in the simulation were calibrated to match the apparatus (which had a roughly 1 meter path from the laser to the test cell). For field applications, the water lines in the region around the $NO_2$ lines would affect the measurements significantly. As a result, de-humidification would need to be performed on samples prior to measurement. Preliminary calculations suggest that passing the sample through a simple gas drying unit using a desiccant, such as anhydrous calcium sulfate, could reduce the humidity level considerably. The effect of residual water vapor in the sample can be further minimized by taking the background spectrum after passing the sample through a good absorber of $NO_2$, such as a long coil of stainless steel. Employing this procedure, the residual water contributions to the spectrum can be subtracted to obtain the concentration of $NO_2$.

To facilitate display of the weak $NO_2$ lines in this region and comparison of their positions to that of the $H_2O$ lines, a simulated $NO_2$ concentration of 5 ppm and a path length of 1000 m were used (this path length is on the order of the effective path length of the CRD cell used in this apparatus). The $H_2O$ spectrum was generated to match typical conditions in the mid-latitude U.S. during the winter months (the time period during which the reported data were recorded). This spectrum was used to select a region with a dense $NO_2$ spectrum that is free from interference due to water lines. The region used for the invention (between 1655.3 $cm^{-1}$ and 1657.3 $cm^{-1}$) is highlighted in the chart of FIG. 3 with a white background.

To maximize the integrated signal, the $NO_2$ concentrations were maintained at a pressure of 1000±100 mbar. Data from 128 scans were averaged using the on-board memory of a Tektronix DPO3034 digitizing oscilloscope 46 (FIG. 1). The oscilloscope output was fed to PC 30 via USB connection and the data was recorded using Tektronix software.

Absorption spectra were recorded for several concentrations of $NO_2$: 1900 ppb, 1350 ppb, 1000 ppb, 750 ppb, 500 ppb, 250 ppb and 0 ppb. By recording the spectra for the weaker lines in the 1655.3 $cm^{-1}$ and 1657.3 $cm^{-1}$ region, the effective concentrations of these mixtures were: 11.9 ppb, 8.4 ppb, 6.3 ppb, 4.7 ppb, 3.1 ppb, 1.6 ppb and 0 ppb. The 0 ppb spectrum was recorded to determine the noise contributions from all components of the test equipment as well as the contributions from the tails of the water lines in the region of interest (due to water vapor in the beam path) and was generated by filling the sample cell with Zero Air.

Figure 4A:
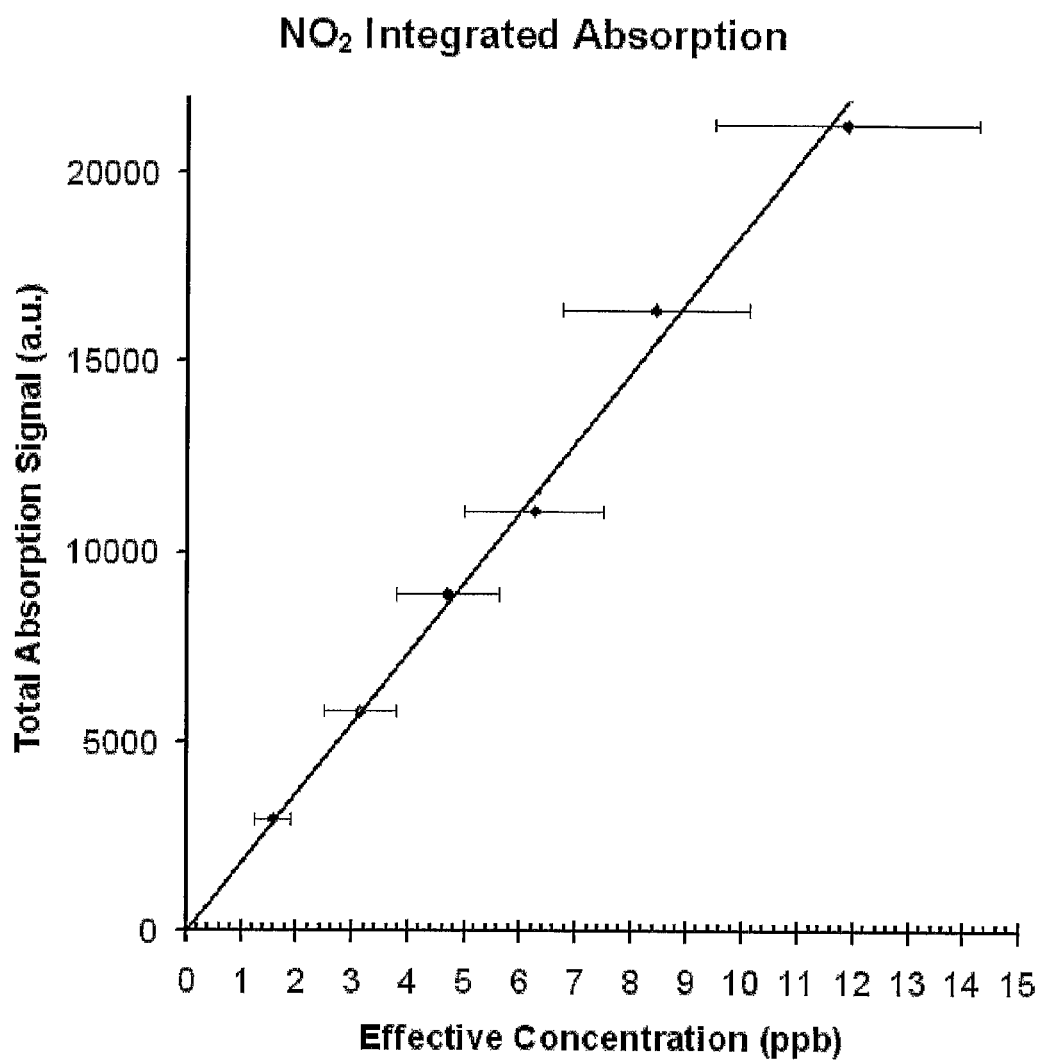
FIG. 4a is a plot of the total absorption signal vs. concentration, as well as a weighted linear least-squares fit of the data.
Figure 4B:
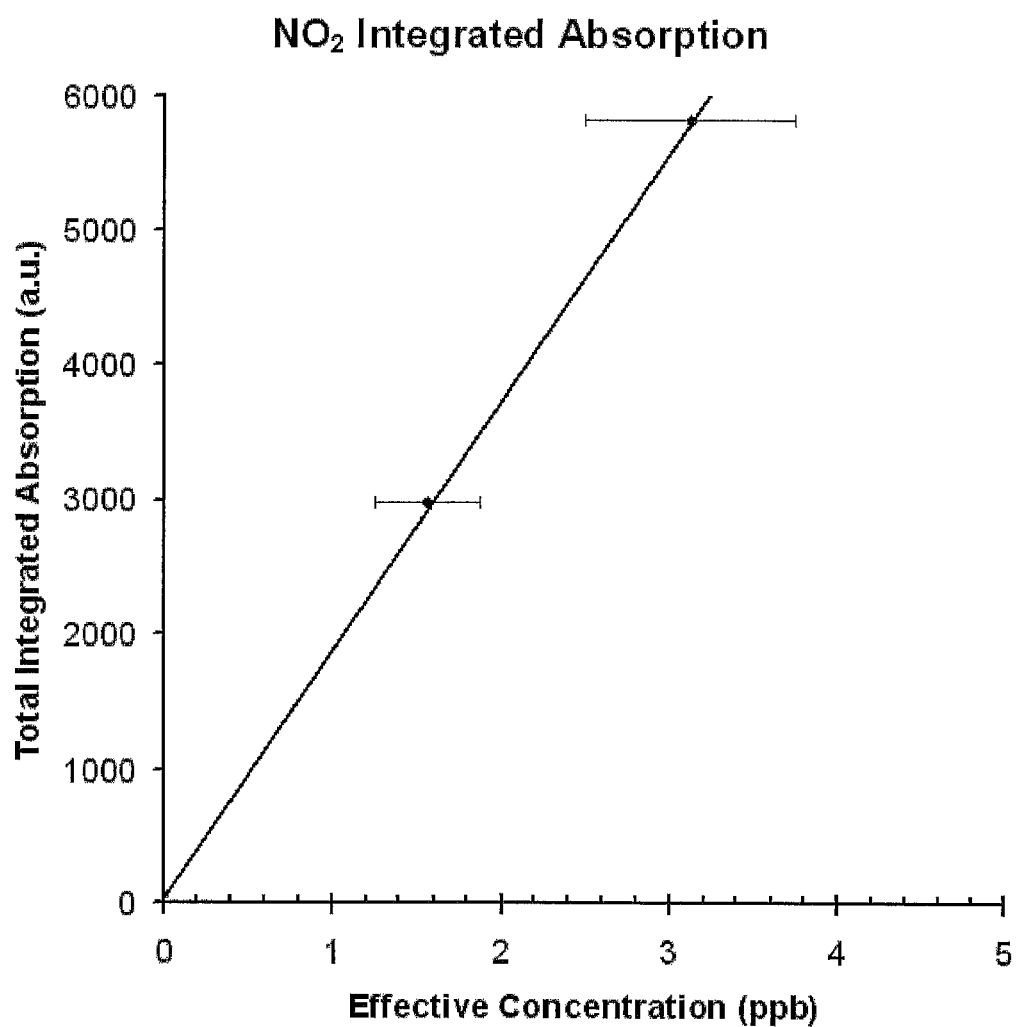
FIG. 4b is the plot of FIG. 4a on an expanded scale to display the low concentration portion of the data.

The data from each spectrum were integrated to yield the total absorption strength $S_T$ for the corresponding concentration. Each of these values was subtracted from the total absorption strength recorded for the 0 ppm concentration; this resulted in the area under the recorded absorption spectrum for the corresponding concentration (which is referred to as the total absorption signal for a given concentration). FIG. 4a shows a plot of the total absorption signal vs. concentration, as well as a weighted linear least-squares fit of this data (the y-axis is given in arbitrary units). FIG. 4b uses an expanded scale to display the low concentration portion of the data. The y-intercept is used to determine the sensitivity of detection.

The instrument's sensitivity is determined using two methods which are in agreement: (1) from the y-intercept of the linear fit and (2) by measuring the standard deviation of the noise spectrum. The y-intercept value of 40 total absorption units is divided by the slope of the fit (1844 total absorption units/ppb) to obtain a sensitivity of approximately 22 ppt. The instrument's sensitivity is also calculated by measuring the standard deviation of the noise spectrum in the integrated absorption signal obtained from a set of repeated measurements on Zero Air. This is accomplished by repeatedly filling the cell with Zero Air, recording the corresponding absorption spectra, determining the integrated absorption signal from these spectra and calculating the standard deviation of the measurements. Using these data the sensitivity of the apparatus is determined to be approximately 28±1 ppt.

This shows an improvement of approximately 4 orders of magnitude over the previous work which employed a simple multiple line integrated absorption spectroscopy (no cavity enhancement) using a short cell of 12.5 cm length and a total path length of 0.88 m and reported a sensitivity of detection of 120 ppb. See the inventors co-pending U.S. patent application Ser. No. 12/878,553 filed on Sep. 9, 2010. The use of ICOS increases the effective path length by over three orders of magnitude over the 88 cm path length used previously. An additional order of magnitude improvement was achieved by averaging 128 scans per concentration, and from reduced uncertainty in the mixed $NO_2$ concentrations through improvements to the gas mixing apparatus.

It should be noted that the present invention is well suited for use as the basis for a field deployable instrument for in-situ trace gas detection. Both the Daylight Solutions QCL and the Vigo detectors are thermo-electrically cooled and thus do not require cryogenics. Alternatively, one can use a diode laser with or without an external cavity arrangement instead of an external cavity quantum cascade laser. Additionally, the use of ICOS makes the apparatus less susceptible to vibrations than other long-path techniques such as cavity ring down spectroscopy and multipass Herriott cells The present invention provides a highly sensitive sensor for trace gas detection by using multiple line integrated absorption spectroscopy and enhancing the effective path length by using off-axis integrated cavity output spectroscopy. This combination of techniques allowed the detection of trace concentrations of $NO_2$ with a high specificity and sensitivity of 28 ppt. This technique can be applied to the detection of a variety of species such as molecules, explosive compounds etc with high sensitivity. However, it should be stated that this technique can significantly improve the sensitivity of detection by several orders of magnitude particularly for the detection of other polyatomic species besides $NO_2$ that have dense rotational-vibrational spectra over a relatively compact frequency range. Though this embodiment was described using a quantum cascade laser with a wide mode hop-free tuning range, the invention can be applied using any tunable laser source, such as a diode laser, capable of tuning across multiple transitions of the target species including complex compounds, such as explosives.

While the invention has been particularly shown and described with reference to a preferred embodiment thereof, it will be understood by those skilled in the art that various changes in form and details may be made therein without departing from the spirit and scope of the invention.

I claim:

1. A method for detecting and measuring the concentration of trace gases using absorption spectroscopy, comprising the steps of:
   generating a pulsed laser beam and employing it in an off-axis configuration so as to generate a high density of transverse cavity modes;
   passing said laser beam into a cavity ring-down type spectroscopy (CRDS) cell containing the trace gas;
   providing an off-axis paraboloidal reflector at the output of the CRDS cell;
   detecting and recording the light beam from the reflector;
   changing the frequency of the laser beam over a desired range of frequencies in which the trace gas has a dense spectrum; and
   integrating the recorded spectra for multiple lines over a desired range of frequencies.

2. The method of claim 1 further including the step of current modulating the laser so that its output frequency is tuned over the absorption features of the species, and averaging over multiple scans, thereby effectively improving the signal to noise ratio.

3. The method of claim 2 wherein the current modulation is created by a current modulator circuit driving the laser head, which is itself driven by a function generator with a high frequency sinusoidal output.

4. The method of claim 1 further including the step of dithering the cavity length of the cell to randomize the cavity modes.

5. A method for detecting and measuring the concentration of trace gases using absorption spectroscopy, comprising the steps of:
  generating a pulsed laser beam and employing it in an off-axis configuration so as to generate a high density of transverse cavity modes;
  passing said laser beam into a cavity ring-down type spectroscopy (CRDS) cell containing the trace gas;
  providing an off-axis paraboloidal reflector at the output of the CRDS cell;
  detecting and recording the light beam from the reflector;
  changing the frequency of the laser beam over a desired range of frequencies in which the trace gas has a dense spectrum;
  integrating the recorded spectra for multiple lines over a desired range of frequencies and
  dithering the cavity length of the-cell to randomize the cavity modes,
  wherein the pulsed laser beam is formed by a quantum cascade laser with fine tuning achieved by a piezo drive of an external cavity grating which in turn is driven by a triangular wave form at a frequency of 3 Hz from a function generator in order to tune the laser over a 2 cm$^{-1}$ range.

6. The method of claim 1 further including the step of dithering the CRD cell length by driving the cell with a piezo driver which in turn is driven by a sinusoid wave form at a frequency of 300 Hz from a function generator.

7. The method of claim 1 wherein the step of detecting the signal is phase locked to the pulses of the laser.

8. The method of claim 1 wherein the gas being detected is $NO_2$.

9. The method of claim 1 wherein the step of changing the laser frequency is achieved by changing an external cavity grating of the laser with a stepper motor.

10. The method of claim 1 wherein the step of changing the laser is achieved by injection current tuning.

11. A method for detecting and measuring the concentration of trace gases using absorption spectroscopy, comprising the steps of:
  generating a pulsed laser beam and employing it in an off-axis configuration so as to generate a high density of transverse cavity modes;
  passing said laser beam into a cavity ring-down type spectroscopy (CRDS) cell containing the trace gas;
  providing an off-axis paraboloidal reflector at the output of the CRDS cell;
  detecting and recording the light beam from the reflector;
  changing the frequency of the laser beam over a desired range of frequencies in which the trace gas has a dense spectrum;
  integrating the recorded spectra for multiple lines over a desired range of frequencies;
  splitting the laser beam so that part of the light enters the CRD cell and part is reflected to a reference cell that does not contain trace gas;
  detecting and recording the laser light after it emerges from the reference cell;
  subtracting the recorded reference cell signal from the recorded CRD cell signal to get a difference signal; and
  integrating by summing the difference signals for multiple lines over a desired range of frequencies.

12. The method of claim 1 wherein the step of generating a pulsed laser beam involves the steps of:
  operating the quantum cascade laser in the continuous wave mode; and
  using an accousto-optical modulator ("AOM") to chop the laser beam into laser pulses.

13. The method of claim 1 wherein the step of generating a pulsed laser beam involves the step of using a pulsed diode laser or a pulsed quantum cascade laser.

14. The method of claim 1 wherein the detected laser beams from the CRD cell are recorded in a lock-in amplifier, additionally amplified and displayed on a fast digital oscilloscope.

15. Apparatus for detecting and measuring the concentration of trace gas species using absorption spectroscopy, comprising:
  a laser source that provides a pulsed laser beam with a frequency tuning range that covers several absorption features of the species of interest;
  a cavity ring-down spectroscopy (CRDS) cell in which the trace gas is located, said CRDS cell having high reflectivity mirrors at the wavelength corresponding to the absorption features of the trace species;
  a reflector for passing said laser beam into the CRDS cell off-axis so as to generate a high density of transverse cavity modes;
  an off-axis paraboloidal reflector at the output of the CRDS cell;
  a photodetector for detecting the laser beam after it is reflected by the reflector and generating a signal related thereto;
  a storage medium for storing the detection signals from the photodetector, and
  an integrator for summing the stored detection signals for multiple lines over a desired segment of frequencies determined by the laser tuning and at the higher harmonics of the modulation frequency of the laser beam.

16. The apparatus of claim 15 wherein the trace gas is $NO_2$.

17. The apparatus of claim 15 further including a first function generator with a high frequency sinusoidal output, and a current modulator circuit driven by the output of the first function generator and driving the laser head so its frequency is modulated, thereby effectively randomizing the mode structure in the cavity.

18. The apparatus of claim 15 further including a second function generator with a low frequency output, and a first piezo driver being driven by the output of the second function generator and driving the laser so as to tune the laser over a desired frequency range.

19. The apparatus of claim 18 wherein the low frequency is a 3 Hz triangle wave form.

20. The apparatus of claim 15 further including a third function generator with a mid frequency output, and a second piezo driver being driven by the output of the third function generator and driving one of the mirrors of the CRD cell to dither the cavity length.

21. The apparatus of claim 20 wherein the mid frequency is a 300 Hz sine wave.

22. The apparatus of claim 15 wherein the laser source is a quantum cascade laser in series with an accousto-optical modulator ("AOM") which chops the light beam into light pulses.

23. The apparatus of claim 15 further including:
a computer that generates a signal driving a stepper motor connected to an external cavity grating of the laser to change its frequency.

24. Apparatus for detecting and measuring the concentration of trace gas species using absorption spectroscopy, comprising:
a laser source that provides a pulsed laser beam with a frequency tuning range that covers several absorption features of the species of interest;
a cavity ring-down spectroscopy (CRDS) cell in which the trace gas is located, said CRDS cell having high reflectivity mirrors at the wavelength corresponding to the absorption features of the trace species;
a reflector for passing said laser beam into the CRDS cell off-axis so as to generate a high density of transverse cavity modes;
an off-axis paraboloidal reflector at the output of the CRDS cell;
a photodetector for detecting the laser beam after it is reflected by the reflector and generating a signal related thereto;
a storage medium for storing the detection signals from the photodetector,
an integrator for summing the stored detection signals for multiple lines over a desired segment of frequencies determined by the laser tuning and at the higher harmonics of the modulation frequency of the laser beam;
a beam splitter intercepting a portion of the light beam before it enters the CRD cell and reflecting it in a different direction;
a reference cell for receiving the light reflected from the beam splitter;
a second photodetector intercepting the light from the reference cell and generating a signal related thereto;
a storage medium for storing the detection signals from the second photodetector;
a subtraction circuit for subtracting the second photodetector signal from the photodetector signal; and
an integrator that sums the difference in the stored detection signals for multiple lines over the desired range of frequencies.

25. The apparatus of claim 15 further including:
a lock-in amplifier connected to the photodetector, said lock-in amplifier including a storage medium for the photodetector;
a second amplifier for amplifying the signal from the lock-in amplifier; and
a digital oscilloscope for displaying the output of the second amplifier.

26. The apparatus of claim 25 wherein the lock-in amplifier and the acousto-optic modulator (AOM) are phase locked.

27. The apparatus of claim 15 wherein the trace gas is $NO_2$ and the desired frequency range is between 1655.3 $cm^{-1}$ and 1657.3 $cm^{-1}$.

* * * * *